(12) United States Patent
Rossow et al.

(10) Patent No.: US 7,645,804 B2
(45) Date of Patent: Jan. 12, 2010

(54) STABLE, CONCENTRATED AND DILUTE, OIL-IN-WATER EMULSIONS, THEIR PROCESSES OF PREPARATION, AND FORMULATION PROCESS EMPLOYING THESE EMULSIONS

(75) Inventors: Véronique Rossow, Arcachon (FR); Nicolas Rossow, Bessancourt (FR); Jean Rossow, Levallois-Perret (FR)

(73) Assignee: J&C International, Gennevilliers (FR)

( * ) Notice: Subject to any disclaimer, the term of this patent is extended or adjusted under 35 U.S.C. 154(b) by 448 days.

(21) Appl. No.: 10/487,786

(22) PCT Filed: Jan. 20, 2004

(86) PCT No.: PCT/FR2004/000122

§ 371 (c)(1),
(2), (4) Date: Aug. 23, 2004

(87) PCT Pub. No.: WO2005/025533

PCT Pub. Date: Mar. 24, 2005

(65) Prior Publication Data

US 2006/0270743 A1    Nov. 30, 2006

(30) Foreign Application Priority Data

Aug. 12, 2003   (FR) ................................. 03 09861

(51) Int. Cl.
*B01F 3/08* (2006.01)
*A23D 7/04* (2006.01)
*A61K 8/06* (2006.01)
*A23D 7/00* (2006.01)

(52) U.S. Cl. ................ 516/53; 516/900; 426/602; 426/612; 426/564; 426/566; 424/401; 514/937; 514/941

(58) Field of Classification Search .............. 516/53, 516/900; 426/474, 519, 602, 603, 604, 611, 426/612, 564, 565, 566, 653; 514/937, 941
See application file for complete search history.

(56) References Cited

U.S. PATENT DOCUMENTS

| | | | | |
|---|---|---|---|---|
| 4,486,333 A | * | 12/1984 | Sebba | ................ 516/14 |
| 5,695,772 A | * | 12/1997 | Kanga et al. | ............. 424/401 |
| 5,798,111 A | * | 8/1998 | Kanga et al. | ............. 424/401 |
| 5,814,313 A | * | 9/1998 | Slavtcheff et al. | ...... 424/78.03 |
| 5,998,536 A | | 12/1999 | Bertry et al. | |
| 6,153,208 A | * | 11/2000 | McAtee et al. | ............. 424/402 |
| 2003/0225166 A1 | | 12/2003 | Gurfinkel Castillo et al. | |

FOREIGN PATENT DOCUMENTS

| | | |
|---|---|---|
| FR | 2 041 400 | 1/1971 |
| FR | 2 738 830 | 3/1997 |
| FR | 2 825 099 | 11/2002 |
| JP | 2002179526 | 6/2002 |
| WO | WO 01/34100 | 5/2001 |
| WO | WO 02 06403 | 1/2002 |
| WO | WO 03 106678 | 12/2003 |

OTHER PUBLICATIONS

H. Sagitani, J. Dispersion Sci., 9, 115 (1988*).
H. Sagitani, Y. Hirai, K. Nabet, Chem. Soc. Jpn, 35, 102 (1986).
Fragrance Journal, 1993-4, 35-40.
Int'l. Preliminary Search Report, dated Mar. 31, 2004, Appl. No. FR 0309861.

* cited by examiner

*Primary Examiner*—Daniel S Metzmaier
(74) *Attorney, Agent, or Firm*—Young & Thompson (57) ABSTRACT

A stable complex oil-in-water emulsion which is useful in the cosmetic, pharmaceutical or food fields. The stable complex oil-in-water emulsion is formed by the mixing of individual oil-in-water emulsions, each individual emulsion being obtained from an air/water pre-emulsion of a preferably-nonionic surfactant; a cosurfactant selected from hydrophilic compounds, preferably with at least one hydroxyl group selected from polyols; and an aqueous phase. A method of preparing a stable complex oil-in-water emulsion whereby individual oil-in-water emulsions, chosen for properties desired in the stable complex oil-in-water emulsion, are optionally diluted and mixed without exerting a shear force.

26 Claims, 2 Drawing Sheets

STABLE, CONCENTRATED AND DILUTE, OIL-IN-WATER EMULSIONS, THEIR PROCESSES OF PREPARATION, AND FORMULATION PROCESS EMPLOYING THESE EMULSIONS

TECHNICAL FIELD

The invention relates to oil-in-water emulsions which exhibit a noteworthy stability and are either concentrated or else dilute, and to their processes of preparation. It also relates to a simple formulation process employing these emulsions.

BACKGROUND OF THE INVENTION

Emulsions are widely used in numerous technical fields, given that they make possible the lasting combination of at least two immiscible liquid-liquid phases.

Emulsions can be classified into two main categories, oil-in-water emulsions and-water-in-oil emulsions. In oil-in-water emulsions, the continuous phase is water; oil droplets are dispersed in this phase. Conversely, in water-in-oil emulsions, the continuous phase is the oil, in which water droplets are dispersed.

In the present application, the term "stable emulsion" is understood to mean an emulsion which does not exhibit phenomena of coalescence or phase separation after storage at ambient temperature for 6 months, preferably after storage at ambient temperature for 12 months and more preferably still at ambient temperature for 18 months.

The qualities required are different depending on the technical field in which the emulsions are employed. However, some qualities are desired for all emulsions, in particular stability over time and towards temperature variations, but also specific qualities in terms in particular of rheology, of stability with respect to pH variations or stability to electrolytes.

In the cosmetic, pharmaceutical or food fields, for example, emulsions have to exhibit numerous additional qualities, in particular in terms of appearance, of compatibility with active substances, of feeling to the touch, of feeling in the mouth, of fragrance, of acceptability with regard to dermatological or food use, and the like.

The emulsions obtained by conventional methods exhibit the disadvantage, however, of being highly sensitive, in particular to temperature and to dilution or to physicochemical parameters, such as the presence of electrolytes or variations in pH.

Any modification, however slight it may be, of the composition of an emulsion can have an influence on its stability and in a way which is difficult to predict. Thus, most of the time, a modification results in a modification in the qualities of the emulsion, indeed even a phase separation of the emulsion, and thus requires the development of a new appropriate formulation process.

Consequently, conventionally, when it is desired to introduce a new product into an emulsion in order to confer a given property or a given appearance thereon or else to increase or reduce the content of one of the constituents, it is necessary to define, by successive trial-and-error experiments, a new complete formulation protocol.

The present inventors have looked for a means for simplifying the work of formulators.

DETAILED DESCRIPTION OF THE INVENTION

After lengthy and detailed research, they have found an extremely simple and extremely practical process for the formulation of complex oil-in-water emulsions which requires a low energy input and results in emulsions exhibiting a noteworthy stability.

This process was disclosed in patent application FR 03/09861 on behalf of the Applicant Company and comprises the stages according to which:
  the properties and functions of the final oil-in-water emulsion desired are determined;
  individual emulsions each exhibiting at least one of the properties or functions which have to be exhibited by the final emulsion are chosen;
  optionally, at least one of the individual emulsions is diluted with an aqueous phase;
  the various individual emulsions, some of which have optionally been diluted beforehand, are mixed;
  the mixture is optionally diluted with an aqueous phase,
the dilution and mixing stages preferably being carried out without exerting shear forces;
each of said individual emulsions being a stable oil-in-water emulsion comprising
  at least one simple or complex fatty substance chosen from the group comprising in particular fatty acid esters, waxes, butters, wax esters, natural, synthetic or mineral oils, hydrogenated oils and their mixtures;
  at least one surfactant, preferably a nonionic surfactant, chosen more particularly from the group consisting of polyglycerol fatty acid esters which are optionally ethoxylated and of alcohol ethoxylates;
  at least one cosurfactant chosen from hydrophilic compounds, preferably comprising at least one hydroxyl group, which are chosen in particular from the family of the polyols;
  water;
  and optionally at least one active agent;

whereby the resulting complex emulsion is stable.

In this patent application, it is indicated that each of the individual emulsions can be prepared by the "detergent phase" process as described in particular in the following articles: Fragrance Journal, 1993-4, 35-40, H. Sagitani, J. Dispersion Sci., 9, 115 (1988), and H. Sagitani, Y. Hirai, K. Nabet, Chem. Soc. Jpn, 35, 102 (1986).

The inventors have now found that this process is very particularly advantageous and effective when each of the individual emulsions is a stable oil-in-water emulsion obtained from an air-in-water preemulsion comprising:
  a surfactant, preferably a nonionic surfactant, chosen more particularly from the group consisting of polyglycerol fatty acid esters which are optionally ethoxylated and of alcohol ethoxylates;

a cosurfactant chosen from hydrophilic compounds, preferably comprising at least one hydroxyl group, which are chosen in particular from the family of the polyols;

an aqueous phase;

in ratios chosen within the region of ordered liquid crystal structure of the phase diagram of these three components and/or in ratios chosen so that the structure of the mixture of these three constituents, observed under an optical microscope in polarized light, exhibits birefringence characteristics, a simple or complex fatty substance being added to said preemulsion by moderate mixing, preferably without exerting a shear force, said fatty substance being chosen from the group comprising in particular fatty acid esters, waxes, butters, wax esters, natural, synthetic or mineral oils, the synthetic oils including in particular silicones and their derivatives, hydrogenated oils and their mixtures.

The emulsion is an oil-in-water emulsion existing in the form of a gel; it is concentrated and very stable and can be diluted.

Within the meaning of the invention, a structure exhibits birefringence characteristics if observation of this structure in polarized light is possible, that is to say if an image is formed. Conversely, the observation in polarized light of a structure not exhibiting birefringence characteristics will be impossible; an image will not be formed and a dark background will be observed.

Figure 1:
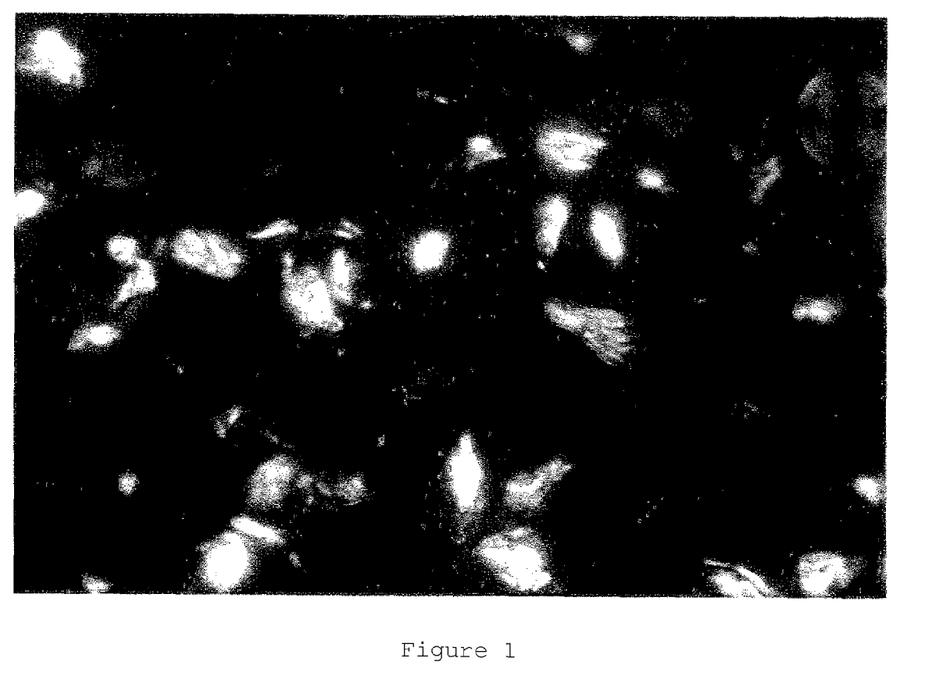
FIG. 1 represents a microscopic view in polarized light of an air-in-water emulsion structure, wherein the required proportions of surfactant, cosurfactant and aqueous phase are illustrated.

The structure of the mixture of surfactant, cosurfactant and aqueous phase in the required proportions as observed under a microscope in polarized light is illustrated in FIG. 1.

The air-in-water preemulsion from which the stable oil-in-water emulsion in accordance with the invention is prepared is a white paste. The air globules (1) constituting this air-in-water emulsion are visible under an optical microscope in polarized light, their surfaces (2) exhibiting birefringence characteristics, as is apparent in FIG. 2.

Without wishing to be committed by any theory, the Applicant Company believes that the structure observed in this figure is a lamellar birefringent ordered structure.

In the present description, the term "oil" generally used denotes oils of vegetable or animal natural origin, of marine origin or of synthetic origin, including in particular silicones and their derivatives, mineral oils, such as liquid paraffins, or hydrogenated oils but also other simple or complex fatty substances, such as, in particular, fatty acid esters, waxes, wax esters, butters, and their mixtures.

The aqueous phase can be water, deionized water, sterilized water, or else an oil-in-water emulsion, or else an aqueous solution in which active agents are diluted, dispersed or suspended. The pH of the aqueous phase can vary within a wide range from pH=2 approximately to pH=10 approximately.

According to a particularly advantageous embodiment of the invention, the surfactant is chosen from the group of the surfactants deriving from glycerol consisting of lecithin derivatives, polyglycerol fatty acid esters which are optionally ethoxylated, preferably decaglycerol fatty acid esters with an HLB of greater than or equal to 13, even more preferably decaglycerol laurate, myristate, stearate, isostearate or oleate, and their mixtures.

Polyglycerol fatty acid esters are particularly appropriate in emulsions intended to come into contact with the skin or mucous membranes as they have very little irritant effect.

For their part, the surfactants based on lecithin derivatives are very useful for emulsions for use in foods.

For its part, the cosurfactant used is chosen from water-soluble compounds, preferably compounds comprising at least one hydroxyl functional group, in particular polyols or their mixtures, preferably diglycerol.

The proportion of water, of surfactant and of cosurfactant is chosen within the region of ordered liquid crystal structure of the phase diagram of these three components and/or so that the structure of the mixture of these three constituents as observed under an optical microscope in polarized light exhibits birefringence characteristics.

Observation under a microscope in polarized light of a mixture of these three constituents in proportions lying outside the region of interest does not allow any structure to be distinguished; there is no birefringence.

The air-in-water emulsion comprises, per 100 parts by weight of water, from 300 to 50, preferably from 200 to 120, parts of surfactant and from 300 to 50, preferably from 180 to 100, parts of cosurfactant.

The air-in-water emulsion can, of course, include additives conventionally used in emulsions, for example stabilizers, pH modifiers or antioxidants.

The oil-in-water emulsion in the gel form can, in addition, comprise at least one water-soluble or fat-soluble active agent. Of course, in the case of a water-soluble active agent, the latter will be present in the aqueous part of the emulsion and, in the case of a fat-soluble active agent, the latter will be present in the oily phase.

The invention also relates to a process for the preparation of a stable oil-in-water emulsion successively comprising:

a. the choice of a surfactant, preferably of a nonionic surfactant, chosen more particularly from the group consisting of polyglycerol fatty acid esters which are optionally ethoxylated and of alcohol ethoxylates, and of a cosurfactant chosen from hydrophilic compounds, preferably comprising at least one hydroxyl group, which are chosen in particular from the family of the polyols;

b. the moderate mixing, preferably without exerting a shear force, of the surfactant, of the cosurfactant and of an aqueous phase in proportions given by the ordered liquid crystal region of the phase diagram of these constituents and/or in proportions chosen so that the structure of the mixture of these three constituents observed under an optical microscope in polarized light exhibits birefringence characteristics, the mixing being carried out until a white air-in-water preemulsion is obtained which is visible by observation under a microscope in polarized light, the surface (2) of the air globules (1) exhibiting birefringence characteristics, as is apparent in FIG. 2;

c. the incorporation in this air-in-water preemulsion of a simple or complex fatty substance by moderate mixing, preferably without exerting a shear force, until a gel is obtained;

d. optionally the addition of an oily phase; and e. optionally the addition of an aqueous phase, so as to obtain a white emulsion.

The simple or complex fatty substance is added in successive fractions with slow stirring without exerting a shear force.

Stage b) of formation of the air-in-water emulsion is monitored by observation under an optical microscope in polarized light. When the constituents, surfactant, cosurfactant and aqueous phase or water, are crudely mixed in the desired proportions, a structure exhibiting birefringence characteristics is observed, the structure being as illustrated in FIG. 1, which is a photograph of the image observed under an optical microscope in polarized light of the crude mixture of the 3 constituents. The presence of this structure, exhibiting birefringence characteristics, is the proof that the proportions between the 3 constituents are satisfactory. Mixing is subsequently continued until the emulsion produced is observed under a microscope to be as illustrated in FIGS. 2a to 2f, that is to say that air bubbles (1) which have surfaces (2) exhibiting birefringence characteristics and which are surrounded by an aqueous phase (3) are observed in polarized light.

Figure 2A:
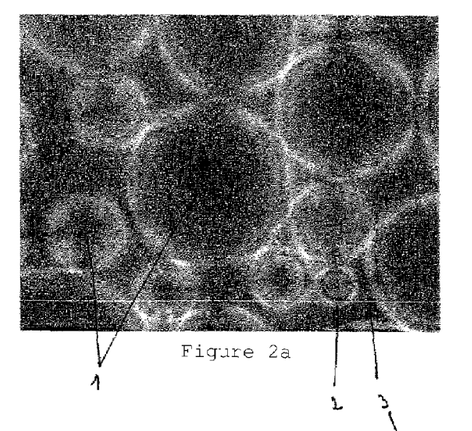
FIGS. 2a to 2f represent the same air-in-water emulsion photographed in different shots.
Figure 2B:
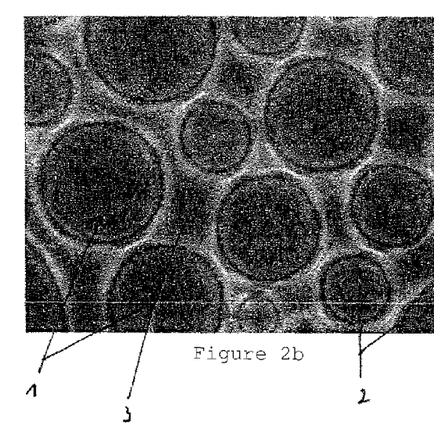
Figures 2C, 2E:
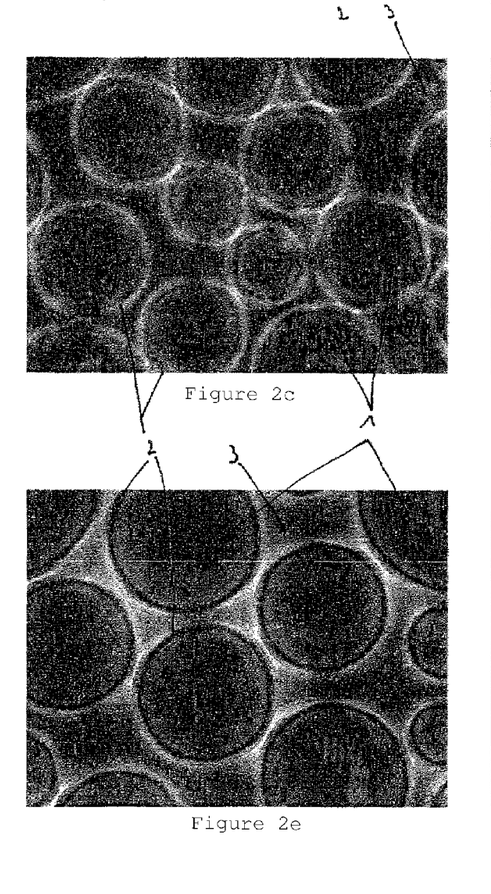
Figure 2D:
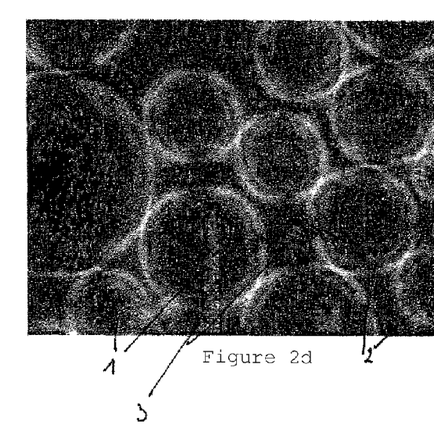
Figure 2F:
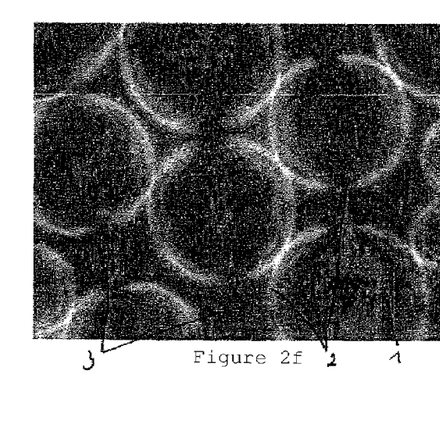

The various FIGS. 2 (2a to 2f) represent the same air-in-water emulsion photographed in different shots (FIGS. 2a to 2e), FIG. 2f corresponding to FIG. 2e but with a different depth of field.

The final white emulsion is obtained by diluting the gel with a simple or complex aqueous phase with gentle stirring and preferably without shearing.

The aqueous phase used in stage e) can be different from that used in stage b) of formation of the air-in-water emulsion.

Within the meaning of the present invention, both the oil-in-water emulsion existing in the gel form obtained on conclusion of stage c) and the white emulsion obtained after addition of an aqueous phase on conclusion of stage e) are referred to as "concentrated emulsions".

In view of the noteworthy stability of the emulsions obtained by the process described above, it is possible to dilute them.

Thus, according to another embodiment, the process according to the invention comprises a subsequent stage f) of dilution generally using an aqueous phase optionally comprising a hydrophilic active substance by mixing said aqueous phase with the stable oil-in-water emulsion obtained previously.

According to yet another embodiment, the process of the invention can comprise, instead of the dilution stage f), before or after the latter, a stage g) of addition by moderate mixing, preferably without shearing, of another stable oil-in-water emulsion according to the invention or of another conventional oil-in-water emulsion.

It is thus possible to mix different stable oil-in-water emulsions of the invention with one another in order to obtain a complex oil-in-water emulsion. The complex oil-in-water emulsion is itself also stable.

The mechanical operation of mixing the various constituent compounds of the air-in-water preemulsion and of the oil-in-water emulsion and of diluting and mixing various individual emulsions is carried out in a moderate fashion, without it being necessary to exert shearing, the latter even being preferably avoided.

This operation is carried out, for example, using an anchor stirrer or a planetary mixer.

Each mixing or dilution stage can be carried out at a temperature below 70° C., preferably below 40° C. and more preferably still at ambient temperature.

The amount of aqueous phase added to the gel in stage e) depends on the type of concentrated emulsion and on its use. This amount represents approximately ⅕ of the formula for an emulsion intended to be: (a) sprayable and with a high content of internal oily phase, or (b) a milk and with a high content of internal oily phase, ¼ of the formula for an emulsion intended to be a cream or milk "excipient emulsion" with a moderate content of oily phase, and ½ of the formula for an emulsion intended to be sprayable and with a moderate to low content of oily phase.

The oil-in-water emulsions obtained at any stage in the process exhibit a noteworthy stability and shared physical characteristics.

The size of the oil particles or droplets varies according to the type of surfactant(s) employed in the stable oil-in-water emulsions of the invention; however, the particle size distribution is homogeneous within an oil-in-water emulsion.

According to an advantageous embodiment, the oil-in-water emulsion is fine, that is to say that the mean diameter of the oil particles or droplets is less than approximately 10 µm, it is generally less than approximately 1 µm and it is preferably between 150 and 750 nm approximately.

The stable oil-in-water emulsions of the invention comprise from 0.05% to 95% by weight of oil, preferably from 30 to 92% by weight of oil.

Advantageously, the content of surfactant in the emulsion in accordance with the invention is at most approximately 20% by weight, preferably at most approximately 10% by weight and more preferably still at most approximately 5% by weight.

In a particularly advantageous way, the emulsions in accordance with the invention are cosmetic, pharmaceutical or food emulsions which respectively comprise at least one agent having a cosmetic, pharmaceutical or food activity.

The emulsion will exhibit one or more characteristic specific properties or functions according to the choice of the oily phase, of the surfactant and/or of the active agent incorporated in the aqueous phase and/or in the oily phase.

Thus, certain emulsions can have characteristic physicochemical properties, for example a given rheology, a specific texture or an aptitude for spreading, and/or sensory properties, in particular a fragrance or a tint or color.

These properties are conferred, for example, by the presence in the emulsion of at least one agent which modifies the physicochemical and/or sensory characteristics of the emulsion which is chosen from the group comprising in particular colorants, rheology agents, texturizing agents, fillers, fragrances or their mixtures.

Other emulsions may possess, for example, a gustatory function or a pharmaceutical, dermatological, cosmetic, and the like, function or activity.

A gustatory function or a function of use for food emulsions is, for example, a specific taste, a flavoring, an improvement in the feeling in the mouth or an enrichment in vitamins or in essential fatty acids.

This function is conferred by a natural or synthetic flavor, a sugaring agent, a salting agent, sweeteners, vitamins, inorganic salts, essential fatty acids, a bitterness agent, a refreshing agent, and the like.

A pharmaceutical function or activity can be conferred by the presence of an active pharmaceutical oil or else of at least one pharmaceutically active substance or else of an agent which makes possible modification of the release of the active substance.

A cosmetic or dermatological function or activity can be an activity in combating ageing, in cicatrization, in limiting the secretion of seborrhea, in cleaning, in protecting against UV radiation, in moisturizing, in emollience, in astringency, and the like.

These functions are introduced by an oily phase which has cosmetic properties and/or by the addition, to the oily or aqueous phase, of active agents, such as an antiwrinkle agent, a UVW screening agent, a moisturizing agent, a tightening agent, an emollient, an astringent agent, a foaming agent, a feel agent, a refreshing agent, vitamins, essential oils, proteins, amino acids, fruit acids, and the like.

Of course, an emulsion can comprise several properties and/or functions.

The amount of active agents which are present in the emulsion according to the invention depends, of course, on their nature. The amount of water-soluble active agents, which are present in the aqueous phase, can vary within a very wide range of values which can extend up to approximately 80% by weight of the total weight of the emulsion; more generally, it is at most approximately 10% and preferably of the order of approximately 5%. The amount of fat-soluble active agents, which are present in the oily phase, can be up to approximately 92% by weight, preferably from 30 to 50% by weight and more preferably still from 1 to 10% by weight of the total weight of the emulsion.

It is possible, among the oil-in-water emulsions in accordance with the invention, to distinguish "excipient" emulsions and "active" emulsions. "Excipient" emulsions play the role of the excipients in conventional formulating; they confer the body or the base of the formula. Their role is not to introduce a special function or property into the final formula. They are used either alone or as formulation body. These formulations are intended to be diluted, either using an aqueous phase, when they are used alone, or else with active emulsions, when they are used as formulation body. In both cases, in order to avoid any creaming phenomenon and to retain a satisfactory viscosity, they can be diluted down to a maximum threshold which depends in particular on the surfactant/cosurfactant system employed and which is at least 50% of the base emulsion in the case of "bases" for sprayable emulsions and at least 40% of the base emulsion in the case of "bases" for creams or for milks. However, these percentages can vary, in particular according to the melting point of the oily phases used for the bases for creams or for milks.

For their part, "active" emulsions are formulated in order to be able to be added to the formula body in the smallest amount possible while introducing the greatest possible effectiveness (that is to say, that the active principle is present in the greatest amount possible).

An additional difficulty for formulators is the preparation of sprayable formulas, that is to say formulas exhibiting a viscosity such that they can be pumped easily and projected as fine droplets.

The present inventors have found that the stable emulsions in accordance with the invention can be provided in the form of sprayable emulsions. The emulsions for sprayable products in accordance with the invention can be prepared in different ways from the concentrated emulsions. These concentrated emulsions are of cream type, that is to say not freely flowing, of milk type, that is to say freely flowing but not directly sprayable, or else of sprayable type.

The feel of the final sprayable emulsion and its final concentration in the oily phase will be different according to the starting concentrated emulsion.

Concentrated emulsions of cream type are rich in oil and comprise from 45 to 90% by weight, of the total weight of the concentrated emulsion, of oil, preferably approximately 68%; they exhibit a surfactant/cosurfactant ratio of between 0.5 and 1.5, preferably approximately 1.22, and a surfactant/oil ratio of between 0.01 and 0.15, preferably approximately 0.05. These oil-rich concentrated emulsions can be diluted down to a minimum content of oil in the sprayable dilute emulsion of between 35% and 70%, preferably approximately 40.0%, by weight.

Concentrated emulsions of milk type can exhibit a moderate oil content and thus comprise from 10 to 70% of oil by weight of the total weight of the concentrated emulsion, preferably approximately 30% in the case where they are formulated based on fatty substances which are solid at ambient temperature, or else they exhibit a high oil content, preferably 68% in the case where they are prepared using fatty substances and surfactants which are liquid at ambient temperature; they generally exhibit a surfactant/cosurfactant ratio of between 0.5 and 2.5, preferably approximately 0.9 to 1.3, and a surfactant/oil ratio generally of between 0.01 and 1. These concentrated emulsions, which have an oil content preferably of 68%, may be sprayable when they are diluted, this being the case down to a minimum content of oil in the sprayable dilute emulsion of between 1 and 60%, preferably approximately 42%, by weight.

Individual sprayable concentrated emulsions exhibiting a low oil content are particularly suited to the preparation of "active" concentrates (which can be sprayed as formulated, even when they have not been diluted) which are intended to be added in small amounts to "excipient" emulsions. They comprise from 1 to 40% of oil by weight of the total weight of the concentrated emulsion, preferably approximately 30%; they exhibit a surfactant/cosurfactant ratio of between 1.5 and 10, preferably approximately 1.05, and a surfactant/oil ratio of between 0.1 and 3, preferably approximately 0.33. These concentrated emulsions with a low oil content can be diluted alone, without creaming phenomena, down to a minimum content of oil in the dilute emulsion of between 0.05 and 10%, preferably approximately 5%, by weight.

The individual emulsions intended to be diluted by an oily phase which exist in the form of gels and are obtained on conclusion of stage c) of the process in accordance with the invention have an oil content of between 10 and 70% of the total weight and preferably of 60%, a surfactant/cosurfactant ratio of 0.01 to 10 and preferably of 0.97 to 1.22, and a surfactant/oil ratio of 0.01 to 0.5 and preferably of 0.17 to 0.27. The amount of oily phase which can be added is from 0.1 to 100%; there is no preferred value as this dilution is carried out according to what the formulator wishes to add.

In view of the fact that the oil-in-water emulsions in accordance with the invention are very stable and can be mixed with one another and that the resulting emulsion is itself very stable and has all the properties, functions and/or characteristics of each of the emulsions which constitute it, with possibly specific synergies when two "active" emulsions are mixed, synergies which can introduce novel properties, in a practical way, it is therefore possible to formulate in a very simple way complex emulsions exhibiting the desired combination of functions, characteristics and properties.

These emulsions are said to be complex as several types of oil particles or droplets are dispersed in a stable way in the aqueous phase, which can itself comprise active agents.

The invention thus also relates to a process for the formulation of a complex oil-in-water emulsion comprising the stages according to which:
- the properties and functions of the final oil-in-water emulsion desired are determined;
- individual emulsions each exhibiting at least one of the properties or functions which have to be exhibited by the final emulsion are chosen;
- optionally, at least one of the individual emulsions is diluted with an aqueous phase;
- optionally, at least one of the specific individual emulsions is diluted with an oily phase;
- the various individual emulsions, some of which have optionally been diluted beforehand, are mixed;
- dilution is optionally carried out with an aqueous phase;
- dilution is optionally carried out with an oily phase;

the dilution and mixing stages preferably being carried out without exerting shear forces;

each of said individual emulsions being a stable oil-in-water emulsion according to the invention.

The mechanical operation of mixing the various individual emulsions is carried out in a moderate way without it being necessary to apply shearing, the latter even being preferably avoided.

This operation is carried out, for example, using an anchor stirrer or a planetary mixer.

Each mixing or dilution stage can be carried out at a temperature below 70° C., preferably below 40° C. and more preferably still at ambient temperature.

The number of individual emulsions which can be combined with one another is not a limiting factor.

However, generally, the formulation process in accordance with the invention comprises the mixing of at most 20 individual emulsions, preferably of at most 10 individual emulsions and even more preferably of 2 to 8 individual emulsions.

In view of the fact that each property or function is contributed by a different individual emulsion and that the different individual emulsions are combined with one another, it is possible to prepare, in accordance with the invention, complex emulsions simultaneously comprising incompatible active agents. They are mainly lipophilic active agents.

The incompatibility of certain active materials with one another is therefore not an obstacle to the formulation of emulsions in accordance with the process of the invention.

In view of this simplicity of formulation, it is possible to install tailor-made formulation terminals or dispensers which allow the consumer to customize existing formulations or else to create specific formulations.

Thus, another aspect of the invention consists of the installation of dispensers which make possible the manufacture of emulsions, in particular of cosmetic emulsions, from instructions captured by a user on a screen or any other dialog system and relating to the qualities, properties or characteristics of the desired emulsion. In addition, the dispenser can be programmed to deliver the emulsion accompanied by its composition in decreasing order of concentration of its various constituents, in order to meet legal requirements.

The present invention also relates to the complex oil-in-water emulsions thus obtained which exhibit a noteworthy stability and can comprise a mixture of incompatible active materials.

It also relates to a process for the preparation of products comprising at least one complex oil-in-water emulsion.

This process comprises the stages composed of the preparation of at least one complex oil-in-water emulsion according to the invention and the mixing of this (or these) emulsion(s) with the other constituents of the product.

When several complex oil-in-water emulsions according to the invention are used, they are advantageously mixed beforehand with one another, before the addition of the other constituents.

The invention will be described in more detail in the following examples, which are given solely by way of illustration of the invention and which are not limiting.

EXAMPLES

In the examples which follow, the oil-in-water emulsions were prepared with a preliminary stage of formation of an air-in-water emulsion.

The protocol for the preparation of the air-in-water emulsion is as follows:

Distilled water, the surfactant and the cosurfactant are mixed without shearing using an anchor stirrer or a planetary mixer.

As soon as these 3 components are brought together and crudely homogenized, a structure exhibiting birefringence characteristics, as illustrated by FIG. 1, is observed under an optical microscope in polarized light. Mixing is continued until a thick white paste is obtained, the appearance of which by observation under a microscope in polarized light is illustrated by FIG. 2, which reveals air bubbles (1) with surfaces (2) exhibiting birefringence characteristics, the interstices (3) between the air bubbles (1) being filled with aqueous phase.

In all the examples, observation under a microscope is carried out in polarized light with an Olympus CX 41 microscope, magnification ×1000.

Example 1

Preparation of a "Cream Base" Emulsion

An oil-in-water emulsion exhibiting the percentage composition given in table 1 below is prepared in the following way.

TABLE 1

| Ingredients | | | % by |
|---|---|---|---|
| Commercial name | Producer | INCI Name | weight |
| Diglycerin S | Sakamoto | Diglycerin | 3.92 |
| S-Face M-1001 | Sakamoto | Polyglyceryl-10 Myristate | 4.8 |
| Parleam | NOF | Hydrogenated Polyisobutene | 46.4 |
| Purester 40 | Strahl & Pitsch | Stearyl Behenate | 8 |
| Coconut Oil | Cognis | Hydrogenated Palm Kernel Oil | 8 |
| Jojoba esters | A&E Connock | Jojoba Esters | 2.4 |
| Lanette 16 | Cognis | Cetyl Alcohol | 3.2 |
| Distilled Water | | Aqua | 23.08 |
| Methylparaben | | Methylparaben | 0.2 |
| Total | | | 100 | a/ Preparation of the Air-in-Water Emulsion 32.8 g of distilled water, 39.2 g of diglycerin and 48 g of polyglyceryl-10 myristate are mixed without shearing, using an anchor stirrer or a planetary mixer, at a temperature slightly greater than the melting temperature of the oily phase.

b/ Preparation of the Oil-in-Water Emulsion

The oily phase, which comprises a mixture of 464 g of hydrogenated polyisobutene, 80 g of stearyl behenate, 80 g of hydrogenated coconut oil, 24 g of jojoba esters and 32 g of cetyl alcohol, is then introduced, with moderate stirring without shearing and at approximately 55° C., every 2.5 minutes approximately in fractions of 10 g four times in succession, then in fractions of 20 g four times in succession and then in fractions of 40 g until incorporation is complete.

When the total amount of oily phase is added, mixing is halted and a gel is obtained.

198 g of distilled water, heated to approximately 55° C., and 2.0 g of methylparaben are added to this gel, still with moderate mixing without shearing.

1 kg of stable white emulsion is obtained, which emulsion does not flow freely after cooling to ambient temperature and which can be diluted with an aqueous phase and/or with an oil-in-water emulsion.

Example 2

Preparation of a "Milk Base" Emulsion

An oil-in-water emulsion exhibiting the percentage composition given in table 2 below is prepared in the following way.

TABLE 2

| Ingredients | | | % by weight |
|---|---|---|---|
| Commercial name | Producer | INCI Name | |
| Diglycerin S | Sakamoto | Diglycerin | 7.84 |
| S-Face S-1001 | Sakamoto | Polyglyceryl-10 Stearate | 9.6 |
| Parleam | NOF | Hydrogenated Polyisobutene | 46.96 |
| Purester 24 | Strahl & Pitsch | Lauryl Laurate | 9.04 |
| Distilled Water | | Aqua | 26.36 |
| Methylparaben | | Methylparaben | 0.2 |
| Total | | | 100 | a/ Preparation of the Air-in-Water Emulsion 65.6 g of distilled water, 78.4 g of diglycerin and 96 g of polyglyceryl-10 stearate are mixed without shearing, using an anchor stirrer or a planetary mixer, at approximately 50° C.

b/ Preparation of the Oil-in-Water Emulsion

The oily phase, which comprises a mixture of 469.6 g of hydrogenated polyisobutene and 90.4 g of lauryl laurate, is then introduced, with moderate stirring without shearing and at approximately 50° C., every 2.5 minutes approximately in fractions of 10 g four times in succession, then in fractions of 20 g four times in succession, then in fractions of 30 g four times in succession and then in fractions of 40 g until incorporation is complete.

When the total amount of oily phase is added, mixing is halted and a gel is obtained.

65.6 g of distilled water, heated beforehand to approximately 50° C., and 2 g of methylparaben are added to this gel, still with moderate mixing without shearing.

1 kg of stable white emulsion is obtained, which emulsion flows freely, is not sprayable and can be diluted with an aqueous phase and/or with an oil-in-water emulsion.

Example 3

Preparation of a Concentrated Emulsion for an "Oil-Rich Sprayable Emulsion"

An oil-in-water emulsion exhibiting the percentage composition given in table 3 below is prepared in the following way.

TABLE 3

| Ingredients | | | % by weight |
|---|---|---|---|
| Commercial name | Producer | INCI Name | |
| Diglycerin S | Sakamoto | Diglycerin | 3.92 |
| S Face IS-1001 | Sakamoto | Polyglyceryl-10 Isostearate | 4.8 |
| Sweet Almond Oil | Bertin | Sweet Almond Oil | 68 |
| Distilled Water | | Aqua | 23.08 |
| Methylparaben | | Methylparaben | 0.2 |
| Total | | | 100 | a/ Preparation of the Air-in-Water Emulsion 32.8 g of distilled water, 39.2 g of diglycerin and 48 g of polyglyceryl-10 isostearate are mixed without shearing, using an anchor stirrer or a planetary mixer, at ambient temperature.

b/ Preparation of the Oil-in-Water Emulsion

The oily phase, which is composed of 680 g of sweet almond oil, is then introduced, with moderate stirring without shearing and at ambient temperature, every 2.5 minutes approximately in fractions of 10 g four times in succession, then in fractions of 20 g four times in succession, then in fractions of 30 g four times in succession and then in fractions of 40 g until incorporation is complete.

When the total amount of oily phase is added, mixing is halted and a transparent gel is obtained.

198 g of distilled water and 2 g of methylparaben are added to this gel, still with moderate mixing without shearing.

1 kg of stable white emulsion is obtained, which emulsion flows freely, is nonsprayable and can be diluted with an aqueous phase and/or with an oil-in-water emulsion.

Example 4

Preparation of a Concentrated Emulsion for a "Sprayable Emulsion with a Moderate to Low Oil Content"

An oil-in-water emulsion exhibiting the percentage composition given in table 4 below is prepared in the following way.

TABLE 4

| Ingredients | | | % by weight |
|---|---|---|---|
| Commercial name | Producer | INCI Name | |
| Diglycerin S | Sakamoto | Diglycerin | 9.5 |
| S-Face M-1001 | Sakamoto | Polyglyceryl-10 Myristate | 10 |
| Sweet Almond Oil | Bertin | Sweet Almond Oil | 30 |
| Distilled Water | | Aqua | 50.3 |
| Methylparaben | | Methylparaben | 0.2 |
| Total | | | 100 | a/ Preparation of the Air-in-Water Emulsion 5 g of distilled water, 95 g of diglycerin and 100 g of polyglyceryl-10 myristate are mixed without shearing, using an anchor stirrer or a planetary mixer, at ambient temperature.

b/ Preparation of the Oil-in-Water Emulsion

The oily phase, which is composed of 300 g of sweet almond oil, is then introduced, with moderate stirring without shearing and at ambient temperature, every 2.5 minutes in fractions of 10 g four times in succession, then in fractions of 20 g four times in succession, then in fractions of 30 g four times in succession and then in fractions of 40 g until incorporation is complete.

When the total amount of oily phase is added, mixing is halted and a gel is obtained.

498 g of distilled water and 2 g of methylparaben are added to this gel, still with moderate mixing without shearing.

1 kg of stable white emulsion is obtained, which emulsion flows freely, can be sprayed and can be diluted with an aqueous phase and/or with an oil-in-water emulsion.

Example 5

Preparation of a Concentrated Emulsion for a "Sprayable Emulsion with a Moderate to Low Content of Oily Phase"

An oil-in-water emulsion exhibiting the percentage composition given in table 5 below is prepared in the following way.

TABLE 5

| Ingredients | | | % by weight |
|---|---|---|---|
| Commercial name | Producer | INCI Name | |
| Glycerol | Dow | Glycerin | 9.5 |
| S Face L 1001 | Sakamoto | Polyglyceryl-10 Laurate | 10 |
| Parleam | NOF | Hydrogenated Polyisobutene | 30 |
| Distilled Water | | Aqua | 50.3 |
| Methylparaben | | Methylparaben | 0.2 |
| Total | | | 100 | a/ Preparation of the Air-in-Water Emulsion 5 g of distilled water, 95 g of glycerol and 100 g of polyglyceryl-10 laurate are mixed without shearing, using an anchor stirrer or a planetary mixer, at ambient temperature.

b/ Preparation of the Oil-in-Air Emulsion 300 g of hydrogenated polyisobutene are then introduced, with moderate stirring without shearing and at ambient temperature, in fractions of 10 g four times in succession, then in fractions of 20 g four times in succession and then in fractions of 30 g for the remaining amount.

A gel is obtained.

503 g of distilled water and 2 g of methylparaben are added to this gel in fractions of 30 to 60 ml, still with moderate mixing without shearing.

1 kg of stable white emulsion is obtained, which emulsion flows freely, is sprayable and can be diluted with an aqueous phase and/or with an oil-in-water emulsion.

Example 6

Preparation of a Concentrated and Dilutable "Antisun" Emulsion

An oil-in-water emulsion exhibiting the percentage composition given in table 6 below is prepared in the following way.

TABLE 6

| Ingredients | | | % by weight |
|---|---|---|---|
| Commercial name | Producer | INCI Name | |
| Diglycerin S | Sakamoto | Diglycerin | 3.92 |
| S-Face M-1001 | Sakamoto | Polyglyceryl-10 Myristate | 4.8 |
| Cranberry Seed Oil | Aromtech | Cranberry Seed Oil | 30 |
| Parsol MCX | Roche Vitamins | Ethylhexyl Methoxycinnamate | 30 |
| Purester 24 | Strahl & Pitsch | Lauryl Laurate | 8 |
| Distilled Water | | Aqua | 23.08 |
| Methylparaben | | Methylparaben | 0.2 |
| Total | | | 100 | a/ Preparation of the Air-in-Water Emulsion 32.8 g of distilled water, 39.2 g of diglycerin and 48 g of polyglyceryl-10 myristate are mixed without shearing, using an anchor stirrer or a planetary mixer, at ambient temperature.

b/ Preparation of the Oil-in-Water Emulsion

The oily phase, which comprises a mixture of 300 g of cranberry seed oil, 300 g of ethylhexyl methoxycinnamate and 80 g of lauryl laurate, is then introduced, with moderate stirring without shearing and at ambient temperature, every 2.5 minutes approximately in fractions of 10 g four times in succession, then in fractions of 20 g four times in succession, then in fractions of 30 g four times in succession and then in fractions of 40 g until incorporation is complete.

When the total amount of oily phase is added, mixing is halted and a gel is obtained.

198 g of distilled water and 2 g of methylparaben are added to this gel, still with moderate mixing without shearing.

1 kg of stable white emulsion is obtained, which emulsion flows freely, is nonsprayable and can be diluted with an aqueous phase and/or with an oil-in-water emulsion.

Example 7

Preparation of a Concentrated Emulsion Which Can Be Diluted With an Oily Phase

An oil-in-water emulsion exhibiting the percentage composition given in table 7 below is prepared in the following way.

TABLE 7

| Ingredients | | | % by weight |
|---|---|---|---|
| Commercial name | Producer | INCI Name | |
| Diglycerin S | Sakamoto | Diglycerin | 9.8 |
| S-Face IS-1001 | Sakamoto | Polyglyceryl-10 Laurate | 6.0 |
| S-Face M-1001 | Sakamoto | Polyglyceryl-10 Myristate | 6.0 |
| Parleam | NOF | Hydrogenated Polyisobutene | 58.7 |
| Purester 24 | Strahl & Pitsch | Lauryl Laurate | 11.3 |
| Distilled Water | | Aqua | 8.0 |
| Methylparaben | | Methylparaben | 0.2 |
| Total | | | 100 | a/ Preparation of the Air-in-Water Emulsion 80 g of distilled water, 98 g of diglycerin, 60 g of polyglyceryl-10 myristate and 60 g of polyglyceryl-10 isostearate are mixed without shearing, using an anchor stirrer or a planetary mixer, at ambient temperature.

b/ Preparation of the Oil-in-Water Emulsion:

The oily phase, which comprises a mixture of 587 g of hydrogenated polyisobutene and 113 g of lauryl laurate, is then introduced, with moderate stirring without shearing and at ambient temperature, every 2.5 minutes in fractions of 10 g four times in succession, then in fractions of 20 g four times in succession, then in fractions of 30 g four times in succession and then in fractions of 40 g the remainder of the 700 g of the oily phase.

When the total amount of oily phase is added, mixing is halted and a transparent gel is obtained.

1 kg of stable transparent gel is obtained, which gel can be diluted with an oily phase and then an aqueous phase or directly with an aqueous phase.

Example 8

Preparation of a Dilutable "Antiwrinkle" Emulsion

An oil-in-water emulsion exhibiting the percentage composition given in table 8 below is prepared in the following way.

TABLE 8

| Ingredients | | | % by weight |
| --- | --- | --- | --- |
| Commercial name | Producer | INCI Name | |
| Glycerol | Dow | Glycerin | 9.5 |
| S-Face M-1001 | Sakamoto | Polyglyceryl-10 Myristate | 10 |
| Bilberry Seed Oil | Aromtech | Bilberry Seed Oil | 30 |
| Purester 24 | Strahl & Pitsch | Lauryl Laurate | 3 |
| Distilled Water | | Aqua | 47.3 |
| Methylparaben | | Methylparaben | 0.2 |
| Total | | | 100 | a/ Preparation of the Air-in-Water Emulsion 5 g of distilled water, 95 g of glycerol and 100 g of polyglyceryl-10 myristate are mixed without shearing, using an anchor stirrer or a planetary mixer, at ambient temperature.

b/ Preparation of the Oil-in-Water Emulsion

The oily phase, which comprises a mixture of 300 g of bilberry seed oil and 30 g of lauryl laurate, is then introduced, with moderate stirring without shearing and at ambient temperature, every 2.5 minutes approximately in fractions of 10 g four times in succession, then in fractions of 20 g four times in succession, then in fractions of 30 g four times in succession and then in fractions of 40 g until incorporation is complete.

When the total amount of oily phase is added, mixing is halted and a gel is obtained.

498 g of distilled water and 2 g of methylparaben are added to this gel, still with moderate mixing without shearing.

1 kg of stable white emulsion is obtained, which emulsion flows freely, can be sprayed and can be diluted.

Example 9

Preparation of a Dilutable "Anti-inflammatory" Emulsion

An oil-in-water emulsion exhibiting the percentage composition given in table 9 below is prepared in the following way.

TABLE 9

| Ingredients | | | % by weight |
| --- | --- | --- | --- |
| Commercial name | Producer | INCI Name | |
| Glycerol | Dow | Glycerin | 9.5 |
| S-Face M-1001 | Sakamoto | Polyglyceryl-10 Myristate | 10 |
| Blackcurrant Seed Oil | Aromtech | Blackcurrant Seed Oil | 30 |
| Purester 24 | Strahl & Pitsch | Lauryl Laurate | 3 |
| Distilled Water | | Aqua | 47.3 |
| Methylparaben | | Methylparaben | 0.2 |
| Total | | | 100 |

The emulsion is prepared in the same way as for example 8, the bilberry seed oil being replaced in the same amounts by the blackcurrant seed oil.

A stable emulsion is obtained which flows freely and which can be sprayed.

Example 10

Preparation of a Dilutable "Cell Regeneration" Emulsion

An oil-in-water emulsion exhibiting the percentage composition given in table 10 below is prepared in the following way.

TABLE 10

| Ingredients | | | % by weight |
| --- | --- | --- | --- |
| Commercial name | Producer | INCI Name | |
| Glycerol | Dow | Glycerin | 9.5 |
| S-Face M-1001 | Sakamoto | Polyglyceryl-10 Myristate | 10 |
| Peat Extract | Aromtech | Peat Extract | 3 |
| Sweet Almond Oil | Bertin | Sweet Almond Oil | 27 |
| Purester 24 | Strahl & Pitsch | Lauryl Laurate | 3 |
| Distilled Water | | Aqua | 47.3 |
| Methylparaben | | Methylparaben | 0.2 |
| Total | | | 100 |

The emulsion is prepared in the same way as for example 8, the bilberry seed oil being replaced by 270 g of sweet almond oil and 30 g of peat extract. A stable white emulsion is obtained which flows freely and which can be sprayed.

Example 11

Dilution of the Base Emulsions

Each of the base emulsions prepared in examples 1 to 5 was diluted with water. The maximum amount of water which it was possible to add for the emulsions to remain "stable", that is to say for there to be no appearance of the creaming phenomenon, is shown in the table below. In all cases, whatever the degree of dilution, none of these emulsions will exhibit phase separation phenomena.

| Base emulsions | Maximum amount of water which can be added (in g per 100 g of concentrate) | Minimum % of oil in dilute emulsions |
| --- | --- | --- |
| Cream base (example 1) | 94 | 35 |
| Milk base (example 2) | 40 | 40 |
| Oil-rich sprayable base (example 3) | 36 | 50 |
| Sprayable base comprising approximately 30% of oil (example 4) | 100 | 15 |
| Sprayable base comprising 30% of oil (example 5) | 400 | 6 |

Specific cases: Example 7: Emulsions dilutable with an oily phase and then dilutions with an aqueous phase

| Oily phase which can be incorporated | Maximum amount of oily phase which can be added (in g per 100 g of concentrate) | Maximum dilution by an aqueous phase of example 7 diluted with an oily phase |
| --- | --- | --- |
| 70:30 Mixture of cyclomethicone (DC 345 from Dow Corning) and lauryl laurate (Purester 24 from Strahl & Pitsch) | 100 | 50% |
| Vitamin A palmitate 1.7 m.i.U./g (Roche) | 20 | 40% |

Example 12

Mixtures of Different Emulsions

Various complex emulsions were prepared by mixing the functional emulsions of examples 6 and 8 to 10 with the base emulsions of examples 1 to 5 and 7.

The minimum amounts of active emulsions which can be mixed with base emulsions for the function of the active emulsion to be displayed by the resulting emulsion are shown in the table below (these values are not limiting and will depend on the composition of the active emulsion).

The maximum amounts which can be added are also shown. These maximum amounts are defined by legal considerations.

| Active emulsions | % minimum | % maximum |
| --- | --- | --- |
| Antisun (ex. 6) | 1 | 25 |
| Antiwrinkle (ex. 8) | 1 | 100 |
| Antiinflammatory (ex. 9) | 1 | 100 |
| Cell regeneration (ex. 10) | 1 | 100 |

Example 13

Formulation of a Moisturizing and Sprayable Body Emulsion

The following individual emulsions are chosen:

(A) emollience and fluid emulsion base (B) silicone (C) citrus fragrance

These individual emulsions are introduced, in the proportions given in table 11 below, into a flask with an aqueous phase comprising water and 0.2% of methylparaben as preservative.

Mixing is then carried out in a moderate fashion until a homogeneous emulsion is obtained. A fluid emulsion is thus obtained, which emulsion can be applied to the skin by spraying, is white in color and is stable.

TABLE 11

| Individual emulsion | % by weight |
| --- | --- |
| A | 20.8 |
| B | 50.0 |
| C | 2.0 |
| Aqueous phase | 27.2 |

The composition of each individual emulsion is given below:

(A) Emollience and fluid emulsion base

| Phases | Commercial name | Producer | INCI Name | % by weight |
| --- | --- | --- | --- | --- |
| A- | Distilled Water | — | Aqua | 3.28 |
|  | Diglycerin S | Sakamoto | Diglycerin | 3.92 |
|  | M-1001 | Sakamoto | Polyglycerol-10 Myristate | 4.8 |
| B- | Parleam | NOF | Hydrogenated Polyisobutene | 68.0 |
| C- | Distilled Water | — | Aqua | 18.8 |
|  | Aristoflex AVC | Clariant | Ammonium Acryloyl-dimethyltaurate/ VP copolymer | 0.2 |
|  | Methylparaben | Tri-K | Methylparaben | 1.0 |

(B) Silicone

| Phases | Commercial name | Producer | INCI Name | % by weight |
| --- | --- | --- | --- | --- |
| A- | Distilled Water | — | Aqua | 3.28 |
|  | Diglycerin S | Sakamoto | Diglycerin | 3.92 |
|  | IS-1001 | Sakamoto | Polyglyceryl-10 Isostearate | 2.4 |
|  | M-1001 | Sakamoto | Polyglycerol-10 Myristate | 2.4 |
| B- | DC 345 | Dow Corning | Cyclomethicone | 48.0 |
|  | Purester 24 | Strahl & Pitsch | Lauryl Laurate | 20.0 |
| C- | Distilled Water | — | Aqua | 19.8 |
|  | Methylparaben | Tri-K | Methylparaben | 0.2 |

(C) Citrus fragrance

| Phases | Commercial name | Producer | INCI Name | % by weight |
|---|---|---|---|---|
| A- | Distilled Water | | Aqua | 3.28 |
| | Diglycerin S | Sakamoto | Diglycerin | 3.92 |
| | S-Face M-1001 | Sakamoto | Polyglyceryl-10 Myristate | 4.8 |
| B- | Lemon fragrance | Fragrance Oils | Fragrance | 16.0 |
| | Parleam 4 | NOF | Hydrogenated Polyisobutene | 4.0 |
| | Purester 24 | Strahl & Pitsch | Lauryl Laurate | 12.0 |
| | Parleam | NOF | Hydrogenated Polyisobutene | 36.0 |
| C- | Distilled Water | | Aqua | 19.8 |
| | Methylparaben | Tri-K | Methylparaben | 0.2 |

Each of the individual emulsions (A) to (C) is prepared in the following way:

The ingredients of phase A are mixed at ambient temperature until an "air-in-water" emulsion is obtained, according to the above protocol.

Phase B is then slowly added with slow stirring and, finally, phase C is added. A fluid and very white oil-in-water emulsion is thus obtained.

The particle size distribution of the resulting emulsion is monodisperse and does not exhibit any coalescence over time.

What is claimed is:

1. A process for the formulation of a complex oil-in-water emulsion, comprising the steps of:
   determining desired gustatory, pharmaceutical, dermatological or cosmetic properties and functions to be exhibited by the complex oil-in-water emulsion;
   choosing at least two individual emulsions, each individual emulsion exhibiting at least one of the properties or functions which are to be exhibited by the complex oil-in-water emulsion;
   optionally diluting at least one of the individual emulsions with an aqueous phase;
   mixing a first individual emulsion exhibiting at least one of the gustatory, pharmaceutical, dermatological or cosmetic properties or functions with at least a second individual emulsion exhibiting at least one of the gustatory, pharmaceutical, dermatological or cosmetic properties or functions, either of which have optionally been diluted beforehand, the mixture of individual emulsions to form a complex oil-in-water emulsion,
   the gustatory property or function being selected from the group consisting of a taste, a flavoring, a feeling in the mouth, an enrichment in vitamins, an enrichment in essential fatty acids,
   the pharmaceutical property or function being a pharmaceutical activity, and
   the dermatological or cosmetic property or function being selected from the group consisting of combating aging, healing, limiting secretion of seborrhea, cleaning, protecting against UV radiation, moisturizing, emmollience, astringency, sunscreen, antiwrinkle, anti-inflammatory and cell regeneration; and
   optionally diluting the mixture of individual emulsions with an aqueous phase,
   each of said individual emulsions being a stable oil-in-water emulsion obtained from an air-in-water preemulsion consisting essentially of a mixture with air of three components:
   a nonionic surfactant,
   a hydrophilic cosurfactant, and
   an aqueous phase,
   the components being present in ratios chosen within a region of ordered liquid crystal structure of the phase diagram of these three components or in ratios chosen so that the structure of the mixture of these three components, observed under an optical microscope in polarized light, exhibits birefringence characteristics, and
   a simple or complex fatty substance being added to said preemulsion by mixing to form a gel, said fatty substance being selected from the group consisting of fatty acid esters, waxes, butters, wax esters, natural, synthetic or mineral oils, hydrogenated oils and mixtures thereof.

2. The process according to claim 1, wherein the air-in-water preemulsion is a white paste, the constituent air globules of which are observed in polarized light, their surfaces exhibiting birefringence characteristics.

3. The process according to claim 1, wherein the air-in-water preemulsion comprises, per 100 parts by weight of water, from 300 to 50 parts of surfactant and from 300 to 50 parts of hydrophilic cosurfactant.

4. The process according to claim 3, wherein the air-in-water preemulsion comprises, per 100 parts by weight of water, from 200 to 120 parts of surfactant and from 180 to 100 parts of hydrophilic cosurfactant.

5. The process according to claim 1, wherein the complex oil-in-water emulsion has a content of nonionic surfactant which is at most approximately 20% by weight.

6. The process according to claim 1, wherein the nonionic surfactant is selected from the group consisting of polyglycerol fatty acid esters, which are optionally ethoxylated, and alcohol ethoxylates.

7. The process according to claim 6, wherein the nonionic surfactant is a decaglycerol fatty acid ester with an HLB of greater than or equal to 13, selected from the group consisting of decaglyceryl laurate, decaglyceryl myristate, decaglyceryl stearate, decaglyceryl isostearate or decaglyceryl oleate, and mixtures thereof.

8. The process according to claim 1, wherein the hydrophilic cosurfactant is a polyol.

9. The process according to claim 8, wherein the hydrophilic cosurfactant is diglycerol.

10. The process according to claim 1, wherein the complex oil-in-water emulsion has an oil content which is between 0.05% and 95% by weight of oil.

11. The process according to claim 1, wherein the complex oil-in-water emulsion comprises oil particles or droplets presenting a mean diameter of less than 10 μm approximately.

12. The process according to claim 1, wherein each of the individual emulsions form the complex oil-in-water emulsion comprises at least one fat-soluble active agent providing the gustatory, pharmaceutical, dermatological or cosmetic properties or function or at least one water-soluble active agent providing the gustatory, pharmaceutical, dermatological or cosmetic properties or function.

13. The process according to claim 1, wherein the complex oil-in-water emulsion comprises water-soluble active agents in the aqueous phase, which are present in an amount that is at most approximately 80% by weight of the total weight of the emulsion, and the complex oil-in-water emulsion comprises fat-soluble active agents in the oily phase, which are present in an amount that is at most approximately 92% by weight of the total weight of the emulsion.

14. A process for the formulation of a complex oil-in-water emulsion, comprising the steps of:
- determining the desired gustatory, pharmaceutical, dermatological or cosmetic properties and functions to be exhibited by the complex oil-in-water emulsion;
- choosing at least two individual emulsions, each individual emulsion exhibiting at least one of the properties or functions which are to be exhibited by the final complex oil-in-water emulsion;
- optionally diluting at least one of the individual emulsions with an aqueous phase;
- mixing a first individual emulsion exhibiting at least one of the gustatory, pharmaceutical, dermatological or cosmetic properties or functions with at least a second individual emulsion exhibiting at least one of the gustatory, pharmaceutical, dermatological or cosmetic properties or functions, either of which have optionally been diluted beforehand, the mixture of individual emulsions to form a complex oil-in-water emulsion,
- the gustatory property or function being selected from the group consisting of a taste, a flavoring, a feeling in the mouth, an enrichment in vitamins, an enrichment in essential fatty acids,
- the pharmaceutical property or function being a pharmaceutical activity, and
- the dermatological or cosmetic property or function being selected from the group consisting of combating aging, healing, limiting secretion of seborrhea, cleaning, protecting against UV radiation, moisturizing, emmollience, astringency, sunscreen, antiwrinkle, anti-inflammatory and cell regeneration; and
- optionally diluting the mixture of the various individual emulsions with an aqueous phase,
- each individual emulsion being a stable oil-in-water emulsion prepared by a process comprising the successive steps of:
  a) choosing a nonionic surfactant and a hydrophilic cosurfactant;
  b) mixing the nonionic surfactant, the hydrophilic cosurfactant and an aqueous phase in ratios chosen within an ordered liquid crystal region of the phase diagram of the nonionic surfactant, the hydrophilic cosurfactant, and the aqueous phase or in ratios chosen so that the structure of the mixture of the nonionic surfactant, the hydrophilic cosurfactant, and the aqueous phase observed under a microscope in polarized light exhibits birefringence characteristics, the mixing being carried out until a white air-in-water preemulsion having air globules surrounded by the aqueous phase is obtained which is visible by observation under a microscope in polarized light, the surface of the air globules exhibiting birefringence characteristics;
  c) incorporating in the air-in-water preemulsion a simple or complex fatty substance by mixing until a gel is obtained.

15. The process according to claim 14, wherein the process for preparing the individual emulsion further comprise a subsequent step of:
  f) diluting using an aqueous phase optionally comprising a water-soluble active agent by mixing.

16. The process according to claim 14, wherein the simple or complex fatty substance is added in successive fractions.

17. The process according to claim 14, wherein each of the individual emulsions has a content of nonionic surfactant which is at most approximately 20% by weight.

18. The process according to claim 14, wherein the surfactant is a nonionic surfactant with an HLB of greater than or equal to 13 selected from the group consisting of polyglycerol fatty acid esters, which are optionally ethoxylated, and alcohol ethoxylates.

19. The process according to claim 14, wherein the cosurfactant is a polyol.

20. The process according to claim 14, wherein each of the individual emulsions has an oil content between 0.05% and 95% by weight of oil.

21. The process according to claim 14, wherein each of the individual emulsions comprises oil particles or droplets presenting a mean diameter of less than 10 μm approximately.

22. The process according to claim 14, wherein each of the individual emulsions comprises at least one fat-soluble active agent or at least one water-soluble active agent.

23. The process according to claim 22, wherein the water-soluble active agents, which are present in the aqueous phase, are at most approximately 80% by weight of the total weight of the emulsion, and the fat-soluble active agents, which are present in the oily phase, are at most approximately 92% by weight of the total weight of the emulsion.

24. The process according to claim 14, wherein the process for preparing the individual emulsion further comprises a subsequent step of
  d) adding an oily phase.

25. The process according to claim 14, wherein the process for preparing the individual emulsion further comprises a subsequent step of
  e) adding an aqueous phase, so as to obtain a white emulsion.

26. The process according to claim 25, wherein the process for preparing the individual emulsion further comprises a subsequent step of:
  g) adding and mixing to the stable oil-in-water emulsion prepared according to steps a) to e) a stable oil-in-water emulsion selected from the group consisting of:
  an oil-in-water emulsion prepared according to steps a) to e), and
  a conventional oil-in-water emulsion not obtained according to steps a) to e).

* * * * *

UNITED STATES PATENT AND TRADEMARK OFFICE
CERTIFICATE OF CORRECTION

PATENT NO. : 7,645,804 B2 Page 1 of 1
APPLICATION NO. : 10/487786
DATED : January 12, 2010
INVENTOR(S) : Rossow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 815 days.

Signed and Sealed this

Sixteenth Day of November, 2010

David J. Kappos
*Director of the United States Patent and Trademark Office*